United States Patent
Janda

(10) Patent No.: US 11,613,535 B2
(45) Date of Patent: Mar. 28, 2023

(54) COMPOUNDS FOR MYC INHIBITION

(71) Applicant: THE SCRIPPS RESEARCH INSTITUTE, La Jolla, CA (US)

(72) Inventor: Kim D. Janda, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 17/258,626

(22) PCT Filed: Jul. 8, 2019

(86) PCT No.: PCT/US2019/040844
§ 371 (c)(1),
(2) Date: Jan. 7, 2021

(87) PCT Pub. No.: WO2020/014144
PCT Pub. Date: Jan. 16, 2020

(65) Prior Publication Data
US 2021/0269430 A1 Sep. 2, 2021

Related U.S. Application Data

(60) Provisional application No. 62/695,496, filed on Jul. 9, 2018.

(51) Int. Cl.
*C07D 417/14* (2006.01)
*C07D 405/04* (2006.01)

(52) U.S. Cl.
CPC ......... *C07D 417/14* (2013.01); *C07D 405/04* (2013.01)

(58) Field of Classification Search
CPC .................. C07D 405/04; C07D 417/14
See application file for complete search history.

(56) References Cited

U.S. PATENT DOCUMENTS

2016/0264560 A1* 9/2016 Vogt .................. A61K 31/4418

OTHER PUBLICATIONS

Jacob et al., "Synthetic molecules for disruption of the MYC protein-protein interface", Bioorganic and Medicinal Chemistry, pp. 4234-4239, Jul. 11, 2018 (Year: 2018).*

* cited by examiner

*Primary Examiner* — Daniel R Carcanague
*Assistant Examiner* — Gillian A Hutter
(74) *Attorney, Agent, or Firm* — Jennifer Kisko; Thomas Fitting

(57) ABSTRACT

There is disclosed a compound, a pharmaceutical composition and a method of cancer treatment with an improved Myc inhibitor compound. More specifically, there is disclosed an improved compound having with improved solubility, improved binding characteristics and better efficacy and therapeutic activity inhibiting c-MYC wherein the improved compound comprises a tri-substituted pyridine having a thiazoyl moiety at position $R^1$ versus an earlier disclosed genus of tri-substituted pyridine structures.

9 Claims, 2 Drawing Sheets

COMPOUNDS FOR MYC INHIBITION

CROSS-REFERENCE TO RELATED APPLICATION

The subject patent application claims the benefit of priority to U.S. Provisional Patent Application No. 62/695,496 (filed Jul. 9, 2018). The full disclosure of the priority application is incorporated herein by reference in its entirety and for all purposes.

TECHNICAL FIELD

The present disclosure provides improved Myc inhibitor compounds, pharmaceutical compositions, and methods for treating cancer with the improved Myc inhibitor pharmaceutical compositions. The present disclosure provides an improved activity small genus of compounds that exhibited surprisingly improved results over a disclosure of compounds (U.S. patent application Ser. No. 15/035,842 filed 10 Dec. 2014, the disclosure of which is incorporated by reference herein). The lead exemplified compound in the prior patent application is termed KJ-Pyr-9 herein. KJ-Pyr-9 exhibited inhibition of transforming capabilities of an oncogenic ATG-MYC virus in chicken embryo fibroblasts (CEF) and those data are used for comparison to the improved compounds disclosed herein. However, KJ-Pyr-9 (or compound 5a) and the related compounds previously described also exhibited only modest solubility (~8 µM). Therefore, there is a need in the art to improve upon the chemical characteristics of the previously disclosed compounds.

BACKGROUND

The v-myc myelocytomatosis viral oncogene homolog (MYC) protein is an essential regulator of cell-cycle progression occupying and apical space in the transcriptome (Adhikary et al., *Nat. Rev. Mol. Cell Biol.* 2005, 6 (8), 635-645). The proto-oncogene c-myc encodes a transcription factor (Myc) that controls cell proliferation. Myc also plays a role in regulating cell cycle, cell growth, angiogenesis, apoptosis, and oncogenesis. MYC is involved in almost all cancers, and a gain of function in MYC is seen in nearly all human cancers. Myc's activity can increase in tumors as a consequence of mutations, chromosomal rearrangements, increased expression, or gene amplification. Elevated or deregulated expression of c-Myc has been detected in a wide range of human cancers and is often associated with aggressive, poorly differentiated tumors. Such cancers include colon, breast, cervical, small cell lung carcinomas, osteosarcomas, glioblastomas, melanoma and myeloid leukemias.

Part of the difficulty in studying MYC is its frenetic mode of action: although having an ephemeral existence, it is able to seemingly affect transcription in both a local and global manner. Moreover, MYC exists as an intrinsically disordered protein (IDP), taking on structure only in the presence of other basic helix-loop-helix leucine zipper (bHLH-LZ) transcription factors of the MAX network (Conacci-Sorrell et al., *Cold Spring Harb. Perspect Med.* 2014, 4 (1), a014357-a014357; and McKeown and Bradner, *Cold Spring Harb. Perspect Med*, 2014, 4 (10), a014266). This lack of structure and instability greatly impairs the ability to structurally or biophysically characterize MYC interactions. In all, these attributes have worked to make MYC an attractive, but elusive target in drug discovery.

SUMMARY

The present disclosure provides a pharmaceutical compound comprising formula (I)

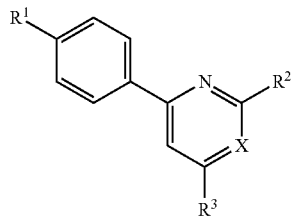

wherein
X is N or CH;
$R^1$ is cyano or thiazolyl;
$R^2$ is 2-furanyl;
$R^3$ is p-$C_6H_4$—$CONH_2$. Preferably, $R^1$ is thiazolyl.

The present disclosure further provides a pharmaceutical composition comprising an effective amount of a compound of formula (I)

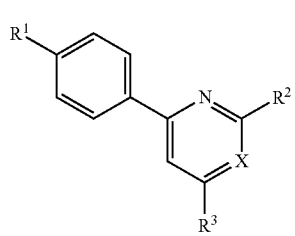

wherein
X is N or CH;
$R^1$ is cyano or thiazolyl;
$R^2$ is 2-furanyl;
$R^3$ is p-$C_6H_4$—$CONH_2$. Preferably, $R^1$ is thiazolyl.

The present disclosure further provides a method for treating a cancer indication, comprising administering an effective amount of a composition comprising formula (I)

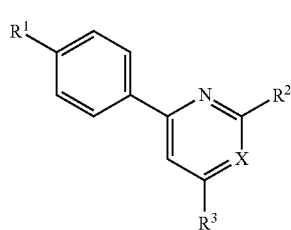

wherein
X is N or CH;
$R^1$ is cyano or thiazolyl;
$R^2$ is 2-furanyl;
$R^3$ is p-$C_6H_4$—$CONH_2$. Preferably, $R^1$ is thiazolyl.

Alternatively, the present disclosure comprises a method of inhibiting MYC-MAX dimerization, comprising contacting the MYC with an effective amount or concentration of a compound of formula (I)

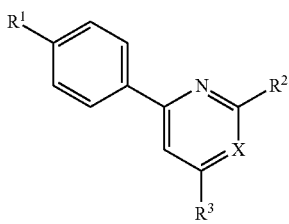

wherein
X is N or CH;
R¹ is cyano or thiazolyl;
R² is 2-furanyl;
R³ is p-C₆H₄—CONH₂.

Further still, the disclosed method inhibits transcriptional activation by MYC, comprising contacting the MYC with an effective amount or concentration of a compound of formula (I)

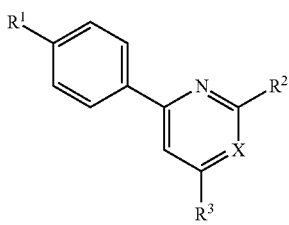

wherein
X is N or CH;
R¹ is cyano or thiazolyl;
R² is 2-furanyl;
R³ is p-C₆H₄—CONH₂.

The invention further provides, in various embodiments, a method of inhibiting MYC-induced cellular proliferation, comprising contacting the MYC with an effective amount or concentration of a compound of formula (I)

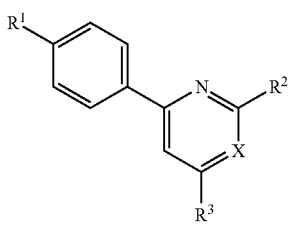

wherein
X is N or CH;
R¹ is cyano or thiazolyl;
R² is 2-furanyl;
R³ is p-C₆H₄—CONH₂.

DETAILED DESCRIPTION

Figure 1:
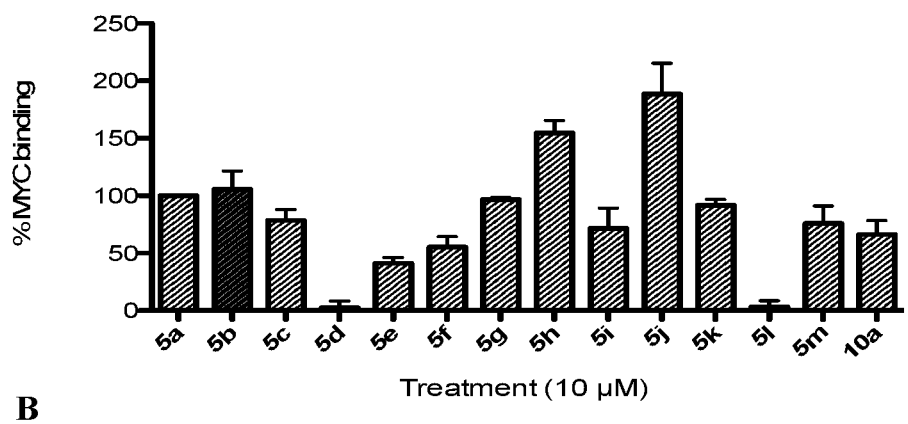
FIG. 1 shows activity screening of test compounds. (A) Relative binding to MYC compared with 5a. (B) Inhibition of MYC-MAX binding to DNA measured by SPR. (C) $IC_{50}$ of optimized compounds in CEF assay.
Figure 1:
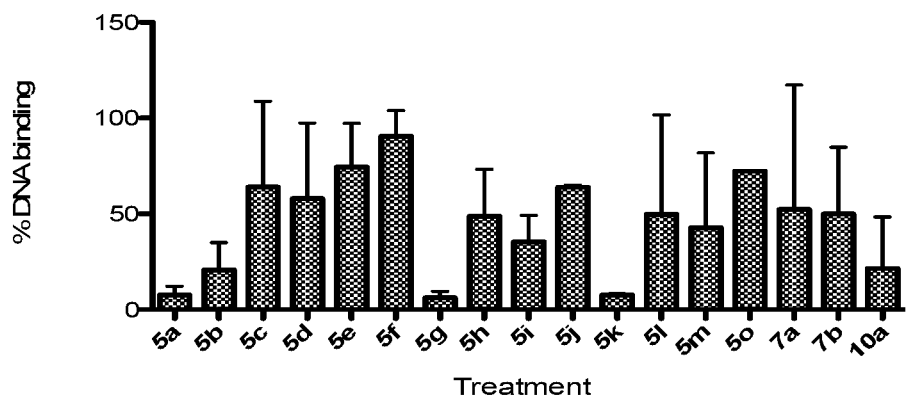
Figure 1:
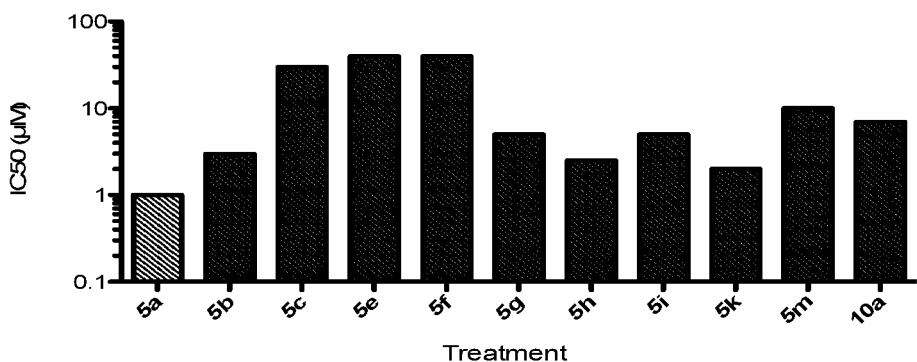

A series of compounds were produced, via a Kröhnke pyridine synthesis, to synthesize a family of α,β-unsaturated ketones 2 using two pathways (Schemes 1a, 1b): For scheme (1a), a reaction of a methyl ketone bearing variety of different five-membered heterocycles such as thiazole, imidazole and triazole or for scheme (1b) an oxazole reaction with the corresponding acylchloride, which allowed for introduction of the oxazole moiety. A second reaction between α,β-unsaturated ketones 2 and pyridinium salts 1 (obtained from the corresponding phenacyl bromide derivative) using ammonium acetate at 100° C. gave the corresponding 2,4,6-trisubstituted pyridines 3. Compounds 5i-k were obtained at this point, while others contained a p-methylester group in the R³ position. The methylester group of 3 was hydrolyzed to obtain carboxylic acid 4. The carboxylic acid was reacted with oxalyl chloride and N,N-dimethylformamide in order to obtain the corresponding acyl chlorides, which were then reacted with different nucleophiles to form compounds 5. In order to access truncated pyridine scaffolds, such as 7a and 7b, a palladium-catalyzed Suzuki cross-coupling strategy was used as shown in Scheme 1b.

After the preparation of these compounds, the next step was to examine their activity relative to prior art compound 5a.

The identities of groups R¹, R², and R³ in Scheme 1a are as follows:
5a: R¹=NO2; R²=2-furanyl; R³=p-C6H4-CONH2
5b: R¹=CN; R²=2-furanyl; R³=p-C6H4-CONH2
5c: R¹=CN; R²=2-thiazolyl; R³=p-C6H4-CONH2
5d: R¹=CN; R²=2-oxazolyl; R³=p-C6H4-CONH2
5e: R¹=CN; R²=N-methyl-2-imidazolyl; R³=p-C6H4-CONH2
5f: R¹=CN; R²=1-methy-1H-1,2,3-triazol-5-yl; R³=p-C6H4-CONH2
5g: R¹=2-thiazolyl; R²=2-furanyl; R³=p-C6H4-CONH2
5h: R¹=5-oxazolyl; R²=2-furanyl; R³=p-C6H4-CONH2
5i: R¹=CN; R²=2-furanyl; R³=C6H5
5j: R¹=2-thiazolyl; R²=2-furanyl; R³=2-thiazolyl
5k: R¹=CN; R²=2-furanyl; R³=p-C6H4-CN4H
5l: R¹=CN; R²=2-furanyl; R³=p-C6H4-CONHMe
5m: R¹=CN; R²=2-furanyl; R³=p-C6H4-CONHSO2Me
5n: R¹=CN; R²=2-furanyl; R³=p-C6H4-CONHNH2
5o: R¹=CN; R²=m-C6H4F; R³=p-C6H4-CONH2

Scheme 1a

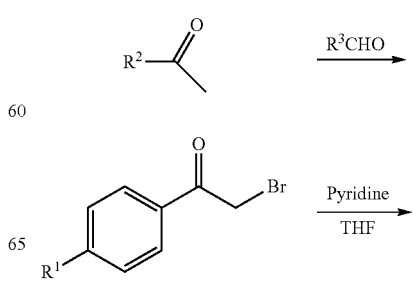

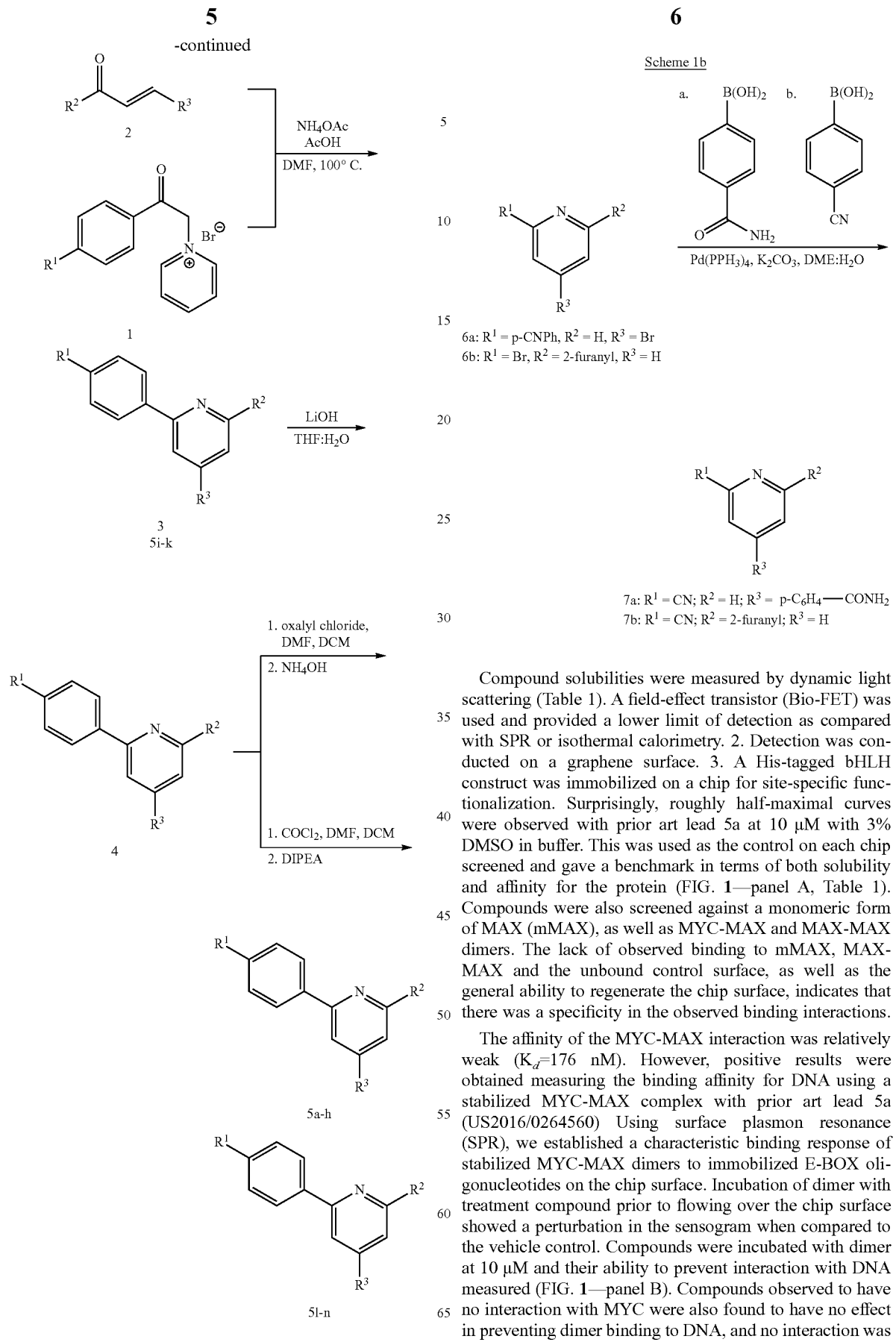

Compound solubilities were measured by dynamic light scattering (Table 1). A field-effect transistor (Bio-FET) was used and provided a lower limit of detection as compared with SPR or isothermal calorimetry. 2. Detection was conducted on a graphene surface. 3. A His-tagged bHLH construct was immobilized on a chip for site-specific functionalization. Surprisingly, roughly half-maximal curves were observed with prior art lead 5a at 10 μM with 3% DMSO in buffer. This was used as the control on each chip screened and gave a benchmark in terms of both solubility and affinity for the protein (FIG. 1—panel A, Table 1). Compounds were also screened against a monomeric form of MAX (mMAX), as well as MYC-MAX and MAX-MAX dimers. The lack of observed binding to mMAX, MAX-MAX and the unbound control surface, as well as the general ability to regenerate the chip surface, indicates that there was a specificity in the observed binding interactions.

The affinity of the MYC-MAX interaction was relatively weak ($K_d$=176 nM). However, positive results were obtained measuring the binding affinity for DNA using a stabilized MYC-MAX complex with prior art lead 5a (US2016/0264560) Using surface plasmon resonance (SPR), we established a characteristic binding response of stabilized MYC-MAX dimers to immobilized E-BOX oligonucleotides on the chip surface. Incubation of dimer with treatment compound prior to flowing over the chip surface showed a perturbation in the sensogram when compared to the vehicle control. Compounds were incubated with dimer at 10 μM and their ability to prevent interaction with DNA measured (FIG. 1—panel B). Compounds observed to have no interaction with MYC were also found to have no effect in preventing dimer binding to DNA, and no interaction was observed between the DNA and compounds alone.

TABLE 1

Activity Summary

| ID | MW | Solubility (μM)[a] | FET R_eq (%)[b] | CEF IC_50 (μM)[c] |
|---|---|---|---|---|
| 5a | 385.4 | 8 | 100 | 1 |
| 5b | 365.4 | 10 | 106 | 3 |
| 5c | 382.4 | 64 | 79 | 30 |
| 5d | 299.3 | 250 | 0 | >100 |
| 5e | 379.4 | 8 | 41 | 40 |
| 5f | 380.4 | 32 | 55 | 40 |
| 5g | 423.5 | 125 | 97 | 5 |
| 5h | 407.4 | 15 | 154 | 2.5 |
| 5i | 366.4 | 2 | 72 | 5 |
| 5j | 387.5 | <1 | 188 | >100 |
| 5k | 390.4 | 18 | 92 | 2 |
| 5l | 379.4 | 25 | 3.2 | NT |
| 5m | 443.5 | 32 | 76 | 10 |
| 5n | 380.4 | 500 | 0 | >100 |
| 5o | 393.4 | 2 | 0 | >100 |
| 7a | 322.4 | 32 | 0 | 10[d] |
| 7b | 246.3 | 10 | 0 | NT |
| 10a | 366.4 | 8 | 66 | 7 |
| 10b | 381.4 | <1 | 0 | >100 |
| 10c | 393.4 | 25 | 0 | >100 |

[a]Measured by DLS in MES (pH 6.0) with <0.1% DMSO.
[b]Relative to 5a $R_{eq}$.
[c]Measured in CEF transfected with ATG-MYC.
[d]inhibited all cell growth.
NT—not tested.

The ultimate assessment of anti-MYC activity was done through a focus assay examining the ability of an ATG-MYC expressing vector to establish microtumors in CEF (Bos et al., *Genes & Development* 1990, 4 (10), 1677-1687.). Active compounds from binding studies were examined for inhibition of microtumor formation in this assay (FIG. 1—panel C). Several new compounds were found to inhibit microtumor formation with similar efficacy to 5a (Table 1).

An α,β-unsaturated ketone 2i was refluxed with furan-carboximidine 8 in the presence of excess sodium methoxide in ethanol to produce carboxylic acid 9, which was converted to the corresponding amide via the strategy of forming acylchloride and reacting it with NH$_4$OH to give pyrimidine 10 (Scheme 2). 10a has an activity profile comparable to 5a.

Scheme 2. Pyrimidine synthesis.

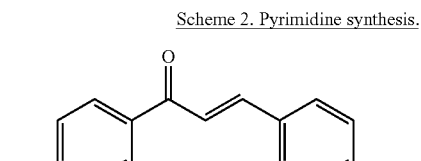

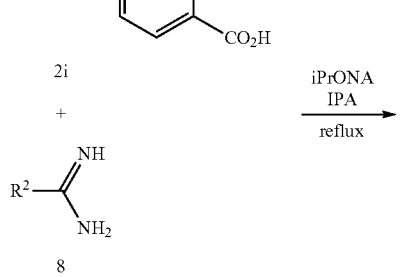

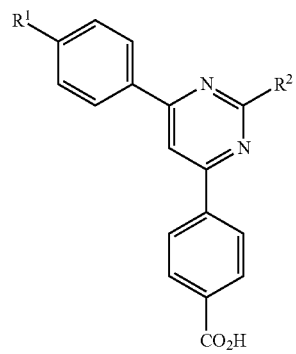

9

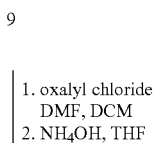

1. oxalyl chloride, DMF, DCM
2. NH$_4$OH, THF

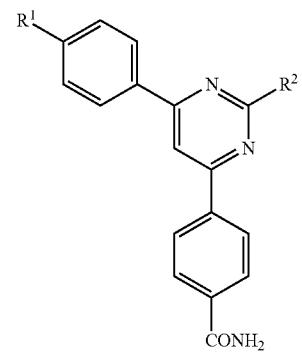

10a: $R^1$ = CN, $R^2$ = 2-furanyl
10b: $R^1$ = OMe, $R^2$ = $C_6H_5$
10c: $R^1$ = CN, $R^2$ = $C_5H_4NO$ Overall, 5g is ideal in that it is readily accessed, has greatly increased solubility, lacks the labile nitro group, and demonstrates similar binding and efficacy to 5a. The affinity of 5g is 12.5±4.1 nM by Bio-FET using a concentration curve. A 10 mg/kg i.v. PK study was conducted in mouse to determine if these favored properties translated into improved PK. Non-compartmental analysis of the mouse PK followed by allometric scaling to the rat afforded a comparison to the rat PK study conducted previously on 5a and is shown in Table 2. This relatively simple substitution has significantly increased the mean residence time from 1 hour to 4.8 producing a 30-fold improvement in exposure (AUC). This demonstrates that there is sufficient plasticity in the chemical space discovered through 5a to improve the physiochemical properties without compromising efficacy.

TABLE 2

PK comparison of 5a (prior art) and 5g (improvement herein).

|  | 5a[a] | 5g[b] |
|---|---|---|
| MW (g/mol) | 385.3 | 423.5 |
| Half-life (h) | 1.0 | 4.8 |
| AUC (ng*h/mL) | 1,450 | 44,000 |
| MRT (h) | 0.94 | 4.3 |

TABLE 2-continued

PK comparison of 5a (prior art) and 5g (improvement herein).

|  | 5a[a] | 5g[b] |
|---|---|---|
| Vss (L) | 6.44 | 0.97 |
| Cl (mL/min/kg) | 115 | 3.8 |

[a] values are allometric scaling of those determined in rat.
[b] values determined in C57B16 mice.

The present disclosure provides a new series of compounds that retain the efficacy of prior art 5a, but with improved in vivo stability and solubility. This is a surprising "goldilocks effect improvement", whereby the hydrophobicity imparted by the conjugation of the scaffold is intrinsically necessary for binding to MYC, but this hydrophobicity negatively affects the pharmacokinetic properties of such a molecule. Thus, the slight activity compromise of 5g for the sake of solubility provides a more drug-like lead compound for targeting MYC.

Therapeutic Applications

The c-Myc inhibitor compound described herein can be useful in various therapeutic or prophylactic (e.g., antitumor) applications, such as, suppressing or inhibiting c-Myc mediated cellular activities, and treating cancers or preventing the development of tumors (particularly MYC-dependent tumors). In some embodiments, the therapeutic applications are directed to preventing development of tumor or treating cancer in a subject. Typically, the therapeutic methods entail administering to a subject a pharmaceutical composition that comprises an effective amount of a c-Myc-inhibiting agent described herein.

The cancers and tumors suitable for treatment with compositions and methods can be those present in a variety of tissues and organs. They also include cancer cells, tumor cells, which include malignant tumor cells, and the like that are found in the component cells of these tissues and/or organs. Examples include brain tumors (glioblastoma multiforme and the like), spinal tumors, maxillary sinus cancer, cancer of the pancreatic gland, gum cancer, tongue cancer, lip cancer, nasopharyngeal cancer, mesopharyngeal cancer, hypopharyngeal cancer, laryngeal cancer, thyroid cancer, parathyroid cancer, lung cancer, pleural tumors, cancerous peritonitis, cancerous pleuritis, esophageal cancer, stomach cancer, colon cancer, bile duct cancer, gallbladder cancer, pancreatic cancer, hepatic cancer, kidney cancer, bladder cancer, prostate cancer, penile cancer, testicular tumors, cancer of the adrenal glands, uterocervical cancer, endometrial cancer, vaginal cancer, vulvar cancer, ovarian cancer, ciliated epithelial cancer, malignant bone tumors, soft-tissue sarcomas, breast cancer, skin cancer, malignant melanomas, basal cell tumors, leukemia, myelofibrosis with myeloid metaplasia, malignant lymphoma tumors, Hodgkin's disease, plasmacytomas, and gliomas.

Generally, the treatment should affect a subject, tissue or cell to obtain a desired pharmacologic and/or physiologic effect. The effect may be prophylactic in terms of completely or partially preventing a disease or sign or symptom thereof. It can also be therapeutic in terms of a partial or complete cure for a disease or disorder (e.g., tumor growth) that is associated with or mediated by abnormal c-Myc expression or biochemical activities, or amelioration of adverse effect that is attributable to the disorder. Suitable subjects include an invertebrate, a vertebrate, a mammal, particularly a human. The c-Myc inhibitor compounds described can be used alone or in conjunction with any of various drugs, including known antitumor drugs (antineoplastic drugs), tumor metastasis-inhibitors, inhibitors for thrombogenesis, therapeutic drugs for joint destruction, analgesics, anti-inflammatory drugs, immunoregulators (or immunomodulators) and/or immunosuppressants, which can be employed as not being restricted to particular species as long as they serve effectively or advantageously.

The compounds can be administered alone to a subject in need of treatment. More preferably, they are administered in the form of a pharmaceutical composition or preparation in admixture with any of various pharmacologically-acceptable additives. For example, the compounds may be administered in the form of a convenient pharmaceutical composition or formulation suitable for oral, topical, parenteral application, or the like. Pharmaceutical compositions of the invention can be prepared in accordance with methods well known and routinely practiced in the art. See, e.g., Remington: *The Science and Practice of Pharmacy*, Mack Publishing Co., 20th ed., 2000; and *Sustained and Controlled Release Drug Delivery Systems*, J. R. Robinson, ed., Marcel Dekker, Inc., New York, 1978. Pharmaceutical compositions are preferably manufactured under GMP conditions. Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for disclosed compounds include ethylene-vinyl acetate copolymer particles, osmotic pumps, implantable infusion systems, and liposomes. Formulations for inhalation may contain excipients, for example, lactose, or may be aqueous solutions containing, e.g., polyoxyethylene-9-lauryl ether, glycocholate and deoxycholate, or may be oily solutions for administration in the form of nasal drops, or as a gel.

Pharmaceutical composition containing a c-Myc-inhibiting compound can be administered locally or systemically in a therapeutically effective amount or dose. They can be administered parenterally, enterically, by injection, rapid infusion, nasopharyngeal absorption, dermal absorption, rectally and orally. The c-Myc inhibitors for use are administered to a subject in an amount that is sufficient to achieve the desired therapeutic effect (e.g., eliminating or ameliorating symptoms associated with tumor development and growth) in a subject in need thereof. Actual dosage levels of the active ingredients in the pharmaceutical compositions can be varied so as to obtain an amount of the active ingredient which is effective to achieve the desired therapeutic response without being toxic to the subject.

The selected dosage level depends upon a variety of pharmacokinetic factors including the activity of the particular compositions employed, the route of administration, the time of administration, and the rate of excretion of the particular compound being employed. It also depends on the duration of the treatment, other drugs, compounds and/or materials used in combination with the particular compositions employed, the age, gender, weight, condition, general health and prior medical history of the subject being treated, and like factors. Methods for determining optimal dosages are described in the art, e.g., Remington: *The Science and Practice of Pharmacy*, Mack Publishing Co., 20th ed., 2000. For a given c-Myc-inhibitor compound, one skilled in the art can identify the effective amount of an agent that inhibits c-Myc by using routinely practiced pharmaceutical methods. Dosages used in vitro or in situ studies may provide useful guidance in the amounts useful for in vivo administration of the pharmaceutical composition, and animal models may be used to determine effective dosages for treatment of particular disorders. Typically, a pharmaceutically effective dosage would be between about 0.001 and 100 mg/kg body weight of the subject to be treated.

The c-Myc inhibitor compounds and other therapeutic regimens described herein are usually administered to the subjects on multiple occasions. Intervals between single dosages can be daily, weekly, monthly or yearly. Intervals can also be irregular as indicated by measuring blood levels of the c-Myc inhibitor compounds and the other therapeutic agents used in the subject. In some methods, dosage is adjusted to achieve a plasma compound concentration of 1-1000 µg/ml, and in some methods 25-300 µg/ml or 10-100 µg/ml. Alternatively, the therapeutic agents can be administered as a sustained release formulation, in which case less frequent administration is required. Dosage and frequency vary depending on the half-life of the c-Myc inhibitor compound and the other drugs in the subject. The dosage and frequency of administration can vary depending on whether the treatment is prophylactic or therapeutic. In prophylactic applications, a relatively low dosage is administered at relatively infrequent intervals over a long period of time. Some subjects may continue to receive treatment for the rest of their lives. In therapeutic applications, a relatively high dosage at relatively short intervals is sometimes required until progression of the disease is reduced or terminated, and preferably until the subject shows partial or complete amelioration of symptoms of disease. Thereafter, the subject can be administered a prophylactic regime.

Examples

All solvents and chemicals were acquired from Thermo-Fisher or Millipore Sigma unless otherwise specified. Solvent was anhydrous unless otherwise specified. Purification of compounds was carried out by prep TLC on 1 mm PLC silica gel 60 $F_{254}$ plates and by flash chromatography on a Teledyne ISCO Combiflash Rf+Lumen. Compounds and intermediates were characterized by NMR on a Bruker DPX-400 or NEO-500 instrument in indicated solvent, and high-resolution mass-spectrometry on an Agilent ESI-TOF. Purity of >95% was determined by HPLC analysis on an Agilent 1260 Infinity (see Supplement). Compounds were screened for known PAINS compounds through 2 database searches (ZINC Patterns, FAF-Drugs4).

Synthetic Methods:

HPLC Analysis. All biologically tested compounds were purified on an Agilent 1260 Infinity instrument. Solvent A is $H_2O$+0.1% TFA, Solvent B is MeCN+0.1% TFA. The method was as follows: a 10 mL/min flow rate was used on a VYDAC C18 column, 5 µm, 10 mm×250 mm with a gradient of 1→95% over 45 min with fractions collected for a 70 min period. Compounds were detected by UV absorption at 250, 254, 210, and 280 nm. Typically, compounds elute at ~55 min. All compounds were assessed to be of 95% of greater purity. LC-MS Analysis. All biologically tested compounds were purified on an Agilent 1260 Infinity 2 instrument with an Agilent InfinityLab LC/MSD. Solvent A is $H_2O$+0.1% TFA, Solvent B is MeCN+0.1% TFA (Honeywell). The method was as follows: a 0.5 mL/min flow rate was used on a ZORBAX 300SB-C8, 5 µm, 4.6×50 mm column with a gradient of 10→95% over 6.5 min with a total run time of 10 min. Compounds were detected by UV absorption at 210, 254, 230, and 280 nm.

Flash Chromatography. Compounds and intermediates were purified on a Teledyne ISCO Combiflash Rf+Lumen instrument using a RediSep 12 g silica column using DCM and methanol. Column was equilibrated with 100.8 mL solvent. Column was run from 0→25% MeOH over 25 mins.

General Procedure for the Synthesis of Phenacyl Pyridinium Salts (1a-c)

1a: 4'-cyano-2-bromoacetophenone (10 g, 45 mmol) was dissolved in THF (150 mL) at room temperature. Then, pyridine (7 mL, 90 mmol) was added and the resulting turbid solution was stirred overnight. The yellow precipitate formed is filtered, washed with ether and dried under vacuum to afford 13 g of the pyridinium salt 1a.

Scheme 3

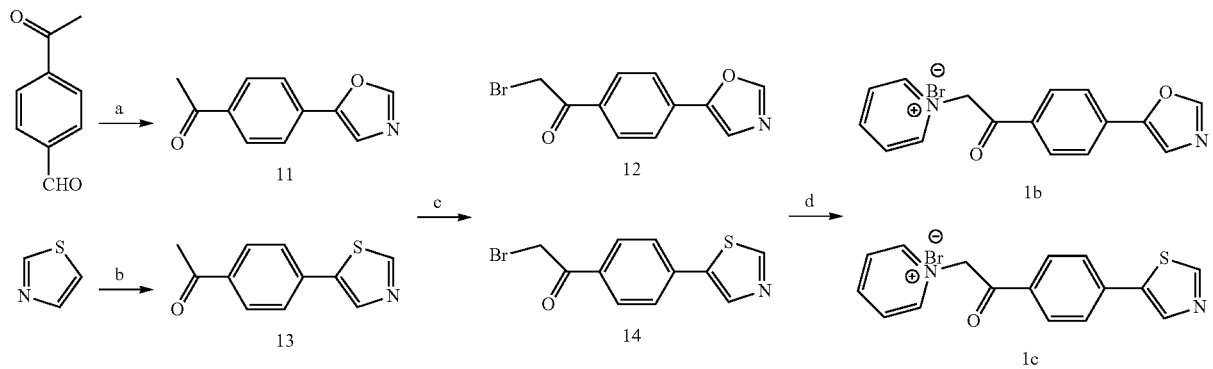

(a) TosMIC, $K_2CO_3$, MeOH; (b) 4-iodoacetophenone, Pd(OAc)$_2$, CuI, DMF, 140 C; (c) TMSBr, NEt$_3$, NBS, DCM; (d) Py, THF 1b: 4-acetylbenzaldehyde (500 mg, 3.4 mmol) and p-toluene sulfonyl methyl isocyanate (800 mg, 3.4 mmol) were dissolved in dry methanol (50 mL). Then, $K_2CO_3$ (560 mg, 3.4 mmol) was added and the mixture was stirred overnight at room temperature. The reaction was extracted with ethyl acetate and water, and the solvent removed under reduced pressure to afford 11 (630 mg, 3.4 mmol). $^1$HNMR (400 MHz, CDCl$_3$): δ=8.01 (d, J=8 Hz, 2H), 7.96 (s, 1H), 7.75 (d, J=8 Hz, 2H), 7.50 (s, 1H), 2.63 (s, 3H).

Oxazole 11 solid was dissolved in dry DCM (100 mL) and bromotrimethylsilane (0.9 ml, 6.8 mmol) followed by triethylamine (1.4 mL, 10 mmol) were added. The reaction was stirred overnight at room temperature. The reaction was washed with water and brine and the organic phase was evaporated under reduced pressure. The resulting dark brown oil was redissolved in dry THF (100 mL) and N-Bromosuccinimide (605 mg, 3.4 mmol) was added. The reaction was stirred at room temperature for 30 min before extracting with ethyl acetate and water. The resulting brown oil was dissolved in DCM and filtered through a pad of silica gel and evaporated to dryness to afford 12 as yellow oil (440 mg, 1.65 mmol). $^1$HNMR (400 MHz, CDCl$_3$): δ=8.04 (d, J=8 Hz, 2H), 7.98 (s, 1H), 7.76 (d, J=8 Hz, 2H), 7.52 (s, 1H), 4.43 (s, 2H).

Bromoderivative 12 was dissolved in THF (6 mL) and pyridine (0.3 mL, 3.3 mmol) and the resulting turbid solution was stirred overnight. The yellow precipitate formed is filtered, washed with ether and dried under vacuum to afford 565 mg of the pyridinium salt 1b. 1c: Thiazole (2.3 mL, 32.52 mmol), 4-iodoacetophenone (4g, 16.26 mmol), copper (I) iodide (6.2 g, 32.52 mmol) and palladium (II) acetate (183 mg, 0.813 mmol) were dissolved in dry DMF (10 mL) in a sealed tube. The reaction mixture is heated at 150° C. for 48 hrs. Then, the solvent reaction mixture was evaporated to dryness and adsorbed over silica gel. The product was purified by silica gel column chromatography using Hex/AcOEt (7:3) as eluent to afford 13 as a yellow solid (2 g, 9.85 mmol). $^1$HNMR (500 MHz, CDCl$_3$): δ=8.07 (d, J=8 Hz, 2H), 8.03 (d, J=8 Hz, 2H), 7.94 (d, J=3 Hz, 1H), 7.43 (d, J=3 Hz, 1H), 2.64 (s, 3H). The solid 13 (1g, 5 mmol) was dissolved in dry DCM (50 mL) and bromotrimethylsilane (1.3 ml, 10 mmol) followed by triethylamine (2 mL, 15 mmol) were added. The reaction was stirred overnight at room temperature. The reaction was washed with water and brine and the organic phase was evaporated under reduced pressure. The resulting dark brown oil was redissolved in dry THF (50 mL) and N-Bromosuccinimide (890 mg, 5 mmol) was added. The reaction was stirred at room temperature for 30 min before extracting with ethyl acetate and water. The resulting brown oil was dissolved in dichloromethane and filtered through a pad of silica gel and evaporated to dryness to afford 14 as yellow oil (1.25 g, 4.4 mmol). $^1$HNMR (600 MHz, CDCl$_3$): δ=8.17-8.05 (m, 4H), 7.98 (d, J=3 Hz, 1H), 7.47 (d, J=3 Hz, 1H), 4.50 (s, 2H).

Bromoderivative 14 (1.25 g, 4.44 mmol.) was dissolved in THF (15 mL) and pyridine (0.85 mL, 9 mmol) was added. The resulting turbid solution was stirred overnight. The yellow precipitate formed is filtered, washed with ether and dried under vacuum to afford 1.8 g of the pyridinium salt 1c.

Synthesis of Compounds 2a-2h

2a: 2-acetylfuran (1.5 g, 13.64 mmol) and LiOH (327 mg, 13.64 mmol) were stirred in MeOH (100 mL) before methyl 4-formylbenzoate (2.2 g, 13.64 mmol) was added. After 30 min a thick colorless precipitate was formed. The precipitate was filtered and dried under vacuum to yield 2a as a colorless solid (70%).

2b: 2-acetylthiazole (2g, 15.72 mmol) and LiOH (376 mg, 15.72 mmol) were stirred in MeOH (100 mL) before methyl 4-formylbenzoate (2.6 g, 15.72 mmol) was added. After 30 min a thick yellowish precipitate was formed. The precipitate was filtered and dried under vacuum to yield 2b as a yellowish solid (73%).

2c: 1-Methyl-2-acetylimidazole (1.8 g, 16.36 mmol) and LiOH (392 mg, 16.36 mmol) were stirred in MeOH (100 mL) before methyl 4-formylbenzoate (2.6 g, 16.36 mmol) was added. After 30 min a thick yellow precipitate was formed. The precipitate was filtered and dried under vacuum to yield 2c as a yellow solid (63%).

2d: 1-(1-methyl-1H-1,2,3-triazol-5-yl)-ethanone (1.9 g, 15.20 mmol) and LiOH (364 mg, 15.20 mmol) were stirred in MeOH (100 mL) before methyl 4-formylbenzoate (2.5 g, 15.20 mmol) was added. After 30 min a thick brownish precipitate was formed. The precipitate was filtered and dried under vacuum to yield 2d as a light orange solid (35%).

2e: To a solution of oxazole (0.1 mL, 1.79 mmol) in THF (10 mL) at −78° C. under a nitrogen atmosphere was added 1.1 equiv of n-BuLi (2.5 M in hexane) (0.85 mL, 2.14 mmol). The resulting solution was stirred for 20 min at −78° C. and 2 equiv of ZnCl$_2$ (1.0 M solution in ether) (4 mL, 3.57 mmol) was added. The mixture was warmed to 0° C. and stirred for 1 hour and 1 equiv of CuI (340 mg, 1.79 mmol) was added. After 10 min 2 equiv of Benzoic acid, 4-(3-chloro-3-oxo-1-propen-1-yl)-methyl ester (800 mg, 3.57 mmol) is added. The reaction was kept at 0° C. until TLC showed complete conversion. The organic solution was diluted with ethyl acetate and washed sequentially with NH$_4$OH/H$_2$O (1:1), water and brine. The product was purified by silica gel chromatography using n-Hex/EtOAc (7:3) to obtain 2e as a white solid (57%). $^1$HNMR (600 MHz, CDCl$_3$): δ=8.11 (d, J=12 Hz, 2H), 8.05 (d, J=12 Hz, 1H), 7.92 (s, 1H), 7.87 (d, J=12 Hz, 1H), 7.77 (d, J=12 Hz, 1H), 7.44 (s, 1H), 3.96 (s, 3H); $^{13}$CNMR (150 MHz, DMSO-d6): δ=175.62, 165.87, 158.48, 144.25, 141.57, 137.94, 131.64, 129.71, 128.85, 128.26, 122.74, 51.89.

2f: 2-acetylfuran (2 g, 18.2 mmol) and benzaldehyde (1.85 mL, 18.2 mmol) were dissolved in ethanol (50 mL). To it, an aqueous solution of 10% NaOH (50 mL) was added and the reaction stirred overnight at room temperature. Then, it was acidified with acetic acid and extracted with ethyl acetate. The resulting oil was purified by column chromatography using as eluent n-Hex/EtOAc (8:2 to 7:3) to obtain 2f as a white solid. (69%).

2g: 2-acetylfuran (1 g, 9 mmol) and LiOH (220 mg, 9 mmol) were stirred in MeOH (50 mL) before 2-thiazolecarboxaldehyde (0.8 mL, 9 mmol) was added. After 30 min a dark brown precipitate was formed. The precipitate was filtered and dried under vacuum to yield 2g as a brown solid (50%).

2h: 2-acetylfuran (316 mg, 2.9 mmol) and LiOH (70 mg, 2.9 mmol) were stirred in MeOH (10 mL) before 4-(1H-tetrazol-5-yl)benzaldehyde (500 mg, 2.9 mmol) was added. After 30 min a yellow precipitate was formed. The precipitate was filtered and dried under vacuum to yield 2h as a yellow solid (71%).

2i: 4-acetylbenzonitrile (435 mg, 3 mmol) and LiOH (72 mg, 3 mmol) were stirred in MeOH (20 mL) before methyl 4-formylbenzoate (500 mg, 3 mmol) was added. After 30 min a yellow precipitate was formed. The precipitate was filtered and dried under vacuum to yield 2i as a yellow solid (56%).

General Procedure for compounds 5a-o. Chalcone 2 (1g, 4 mmol.), and NH$_4$OAc (9.2 g, 120 mmol) were dissolved in a mixture of acetic acid (20 mL) and DMF (30 mL). To it, pyridinium salt 1 (1.2 g. 4 mmol) was added and the reaction mixture was heated at 100° C. overnight. Solvent was evaporated under vacuum and the remaining brown oil was dissolved in DCM (100 mL) and solid NaHCO$_3$ was added until the gas release ceased. The organic phase was dried over MgSO$_4$ and evaporated under reduced pressure. The product 3 is crashed out using Et$_2$O-MeOH as a brown solid. This material was carried on without further purification. LiOH (2.5 g, 104 mmol) was added to a solution of 3 in THF:H$_2$O (9:1) and stirred overnight. The reaction mixture was filtered through a pad of silica gel and evaporated to dryness to afford carboxylic acid 4. 4 (3g, 8.2 mmol.) was dissolved in dry DCM (100 mL) and oxalyl chloride (0.7 mL, 8.2 mmol) followed by 1 drop of DMF. The reaction was stirred at room temperature overnight, then the solvent was removed in vacuo and the remaining solid was redissolved in dry DCM (100 mL). The solution was poured onto a NH$_4$OH solution (50 mL) and the reaction mixture was stirred for 30 min. The organic layer was separated, dried and evaporated under vacuo to afford a brown oil which was purified to obtain pyridine 5.

5b: $^1$HNMR (600 MHz, DMSO-d$_6$): δ=8.54 (d, J=12 Hz, 2H), 8.35 (s, 1H), 8.12 (m, 3H), 8.08 (d, J=6 Hz, 2H), 8.04 (d, J=12 Hz, 2H), 7.94 (s, 1H), 7.50 (brs, 1H), 7.42 (s, 1H), 6.75 (s, 1H); $^{13}$CNMR (150 MHz, DMSO-d$_6$): δ=167.23, 154.81, 152.78, 149.39, 148.74, 144.66, 142.48, 139.50, 134.99, 132.70, 128.25, 127.77, 127.19, 118.83, 117.28, 115.59, 112.48, 111.77, 110.14; HRMS (ESI-TOF): m/z calculated for C$_{24}$H$_{17}$N$_3$O$_2$: 366.1237 (M+H)+; found: 366.1238.

5c: $^1$HNMR (600 MHz, DMSO-d$_6$): δ=8.54 (m, 3H), 8.47 (d, J=12 Hz, 1H), 8.16 (brs, 1H), 8.15 (d, J=6 Hz, 2H), 8.10-8.07 (m, 5H), 8.00 (d, J=6 Hz, 1H), 7.51 (brs, 1H); $^{13}$CNMR (150 MHz, DMSO-d$_6$): δ=167.98, 167.20, 155.01, 151.43, 149.35, 144.47, 141.78, 139.12, 135.21, 132.87, 128.35, 127.75, 127.27, 123.37, 119.94, 118.76, 116.21, 112.08; HRMS (ESI-TOF): m/z calculated for C$_{22}$H$_{14}$N$_{4a}$OS: 383.0961 (M+H)$^+$; found: 383.0960.

5d: $^1$HNMR (600 MHz, DMSO-d$_6$): δ=8.58 (s, 1H), 8.56 (d, J=6 Hz, 2H), 8.44 (s, 1H), 8.41 (s, 1H), 8.16 (brs, 1H), 8.15 (d, J=6 Hz, 2H), 8.09 (d, J=6 Hz, 2H), 8.06 (d, J=6 Hz, 2H), 7.56 (s, 1H), 7.51 (s, 1H); $^{13}$CNMR (150 MHz, DMSO-d$_6$): δ=167.19, 159.87, 155.32, 149.11, 146.41, 142.04, 141.50, 138.94, 135.23, 132.80, 128.99, 128.35, 127.90, 127.28, 120.01, 119.00, 118.75, 112.03; HRMS (ESI-TOF): m/z calculated for C$_{22}$H$_{14}$N$_4$O$_2$: 367.1189 (M+H)+; found: 367.1183.

5e: $^1$HNMR (600 MHz, DMSO-d$_6$): δ=8.51 (d, J=6 Hz, 2H), 8.45 (d, J=6 Hz, 1H), 8.41 (d, J=1.5 Hz, 1H), 8.15 (brs, 1H), 8.09 (d, J=3 Hz, 4H), 8.03 (d, J=6 Hz, 2H), 7.96 (d, J=12 Hz, 2H), 7.50 (brs, 1H), 7.42 (s, 1H), 7.11 (d, J=1 Hz, 1H), 4.23 (s, 3H); $^{13}$CNMR (150 MHz, DMSO-d$_6$): δ=167.25, 154.25, 151.18, 148.53, 143.60, 142.73, 139.54, 135.02, 132.83, 132.38, 128.36, 128.00, 127.09, 125.79, 119.09, 118.81 117.64, 111.75, 36.47; HRMS (ESI-TOF): m/z calcd for C$_{23}$H$_{17}$N$_5$O: 380.1506 (M+H)+; found: 380.1504.

5f: $^1$HNMR (600 MHz, DMSO-d$_6$): δ=8.60 (s, 1H), 8.53 (d, J=6 Hz, 2H), 8.50 (s, 1H), 8.36 (s, 1H), 8.20 (d, J=6 Hz, 2H), 8.16 (brs, 1H), 8.09 (d, J=12 Hz, 2H), 8.05 (d, J=12 Hz, 2H), 7.53 (brs, 1H), 4.50 (s, 3H); $^{13}$CNMR (150 MHz, DMSO-d$_6$): δ=167.18, 155.05, 149.18, 147.61, 142.36, 139.00, 135.62, 135.17, 134.48, 132.85, 128.20, 127.91, 127.39, 120.20, 119.50, 118.75, 118.45, 112.0, 37.96; HRMS (ESI-TOF): m/z calculated for C$_{22}$H$_{16}$N$_6$O: 381.1458 (M+H)+; found: 381.1457.

5g: $^1$HNMR (600 MHz, DMSO-d$_6$): δ=8.46 (d, J=12 Hz, 2H), 8.28 (s, 1H), 8.16 (brs, 1H), 8.12 (m, 3H), 8.08 (d, J=12 Hz, 2H), 8.00 (d, J=3 Hz, 1H), 7.94 (s, 1H), 7.86 (s, d, J=3 Hz, 1H), 7.51 (brs, 1H), 7.40 (s, 1H), 6.75 (s, 1H); $^{13}$CNMR (150 MHz, DMSO-d$_6$): δ=167.29, 166.58, 155.80, 153.00, 149.26, 148.55, 144.50, 144.08, 139.78, 139.67, 134.90, 133.78, 128.77, 127.77, 127.13, 126.48, 120.88, 116.62, 114.92, 112.43, 109.89; HRMS (ESI-TOF): m/z calculated for C$_{25}$H$_{17}$N$_3$O$_2$S: 424.1114 (M+H)+; found: 424.1116.

5h: $^1$HNMR (600 MHz, DMSO-d$_6$): δ=8.52 (s, 1H), 8.45 (d, J=12 Hz, 2H), 8.27 (s, 1H), 8.15 (brs, 1H), 8.12 (m, 3H), 8.04 (s, 1H), 7.93 (m, 3H), 7.94 (s, 1H), 7.84 (s, 1H), 7.50 (brs, 1H), 7.39 (s, 1H), 6.74 (s, 1H); $^{13}$CNMR (150 MHz, DMSO-d$_6$): δ=167.28, 155.89, 153.03, 152.14, 150.21, 149.21, 148.51, 144.48, 139.81, 138.18, 134.88, 128.25, 128.17, 127.68, 127.13, 124.35, 122.81, 116.45, 114.76, 112.42, 109.84; HRMS (ESI-TOF): m/z calculated for C$_{25}$H$_{17}$N$_3$O$_3$: 408.1343 (M+H)+; found: 408.1350.

5i: $^1$HNMR (600 MHz, CDCl$_3$): δ=8.28 (d, J=12 Hz, 2H), 7.96 (s, 1H), 7.85 (s, 1H), 7.82 (d, J=12 Hz, 2H), 7.78 (d, J=6 Hz, 2H), 7.61 (s, 1H), 7.58-7.52 (m, 3H), 7.27 (s, 1H), 6.62 (s, 1H); $^{13}$CNMR (150 MHz, CDCl$_3$): δ=154.94, 153.20, 150.02, 149.62, 143.12, 142.98, 137.76, 132.07, 128.92, 128.75, 127.18, 126.63, 118.43, 116.77, 115.67, 112.07, 111.76, 109.01; HRMS (ESI-TOF): m/z calculated for C$_{22}$H$_{14}$N$_2$O: 323.1179 (M+H)+; found: 323.1182.

5j: $^1$HNMR (600 MHz, DMSO-d$_6$): δ=8.37 (d, J=12 Hz, 2H), 8.31 (s, 1H), 8.15 (s, 1H), 8.12 (s, 1H), 8.11 (d, J=12 Hz, 2H), 8.05 (d, J=6 Hz, 1H), 8.00 (d, J=6 Hz, 1H), 7.94 (s, 1H), 7.86 (s, 1H), 7.37 (s, 1H), 6.74 (s, 1H); $^{13}$CNMR (150 MHz, DMSO-d$_6$): δ=166.48, 164.37, 156.18, 152.55, 149.47, 144.83, 144.51, 144.09, 141.89, 139.04, 133.99, 127.67, 126.58, 123.05, 120.95, 114.96, 113.28, 112.53, 110.20; HRMS (ESI-TOF): m/z calcd for C$_{21}$H$_{13}$N$_3$OS$_2$: 388.0573 (M+H)+; found: 388.0574.

5k: $^1$HNMR (600 MHz, DMSO-d$_6$): δ=8.54 (d, J=12 Hz, 2H), 8.34 (s, 1H), 8.18 (d, J=12 Hz, 2H), 8.11 (s, 1H), 8.07 (d, J=12 Hz, 2H), 8.03 (d, J=12 Hz, 3H), 7.94 (s, 1H), 7.41 (s, 1H), 6.74 (s, 1H); $^{13}$CNMR (150 MHz, DMSO-d$_6$): δ=160.11, 154.69, 152.94, 149.45, 149.31, 144.53, 142.68, 135.00, 134.00, 132.68, 127.74, 127.26, 126.28, 118.86, 116.79, 115.05, 112.42, 111.64, 109.90; HRMS (ESI-TOF): m/z calculated for C$_{23}$H$_{14}$N$_6$O: 391.1302 (M+H)+; found: 391.1315.

Scheme for Synthesis of Compounds 5m-5o

Carboxylic acid 4a (1g, 2.7 mmol.) was dissolved in dry DCM (100 mL) and oxalyl chloride (0.5 mL, 5 mmol) followed by DMF (1 drop) were added. The reaction was stirred at room temperature overnight. Then, the solvent was removed in vacuo and the remaining solid was redissolved in dry DCM (100 mL). The solution was poured onto a solution of (a) methylamine and DIPEA (1:1) (25 mL); (b) methanesulfonamide (300 mg, 3.15 mmol) and DIPEA (10 mL) or (c) hydrazine and DIPEA (1:1) (25 mL) and the reaction mixture was stirred for 30 min. Then, the organic layer was washed with water, separated, dried and evaporated under vacuo to afford 5l, 5m and 5n respectively. The products were purified by prep TLC using DCM/MeOH (85:15) as eluent.

5l: $^1$HNMR (600 MHz, DMSO-d$_6$): d=8.63 (m, 2H), 8.53 (d, J=12 Hz, 2H), 8.35 (s, 1H), 8.14 (d, J=12 Hz, 2H), 8.11 (s, 1H), 8.04 (m, 3H), 7.94 (s, 1H), 7.42 (s, 1H), 6.74 (s, 1H), 2.84 (s, 3H); $^{13}$CNMR (150 MHz, DMSO-d6): d=165.92, 154.82, 152.78, 149.39, 148.70, 144.66, 142.48, 139.29, 135.19, 132.70, 127.83, 127.77, 127.24, 118.83, 117.25, 115.55, 112.48, 111.77, 110.13; HRMS (ESI-TOF): m/z calcd for C$_{24}$H$_{17}$N$_3$O$_2$: 380.1393 (M+H)+; found: 380.1394.

5m: $^1$HNMR (600 MHz, DMSO-d6): d=8.54 (d, J=6 Hz, 2H), 8.32 (s, 1H), 8.12 (d, J=6 Hz, 2H), 8.08 (s, 1H), 8.01 (m, 4H), 7.94 (brs, 1H), 7.93 (s, 1H), 7.40 (s, 1H), 6.74 (m, 1H), 2.89 (s, 3H); $^{13}$CNMR (150 MHz, DMSO-d6): d=169.75, 154.73, 152.86, 149.32, 144.57, 142.58, 140.75, 137.93, 132.68, 129.74, 129.00, 127.76, 126.34, 118.85, 117.10, 115.40, 112.43, 111.68, 109.98, 43.13; HRMS (ESI-TOF): m/z calculated for C$_{24}$H$_{17}$N$_3$O$_4$S: 444.1012 (M+H)+; found: 444.1017.

5n: $^1$HNMR (600 MHz, DMSO-d6): d=9.96 (s, 1H), 8.54 (d, J=12 Hz, 2H), 8.35 (s, 1H), 8.14 (d, J=6 Hz, 2H), 8.11 (s, 1H), 8.03 (d, J=12 Hz, 3H), 7.94 (s, 1H), 7.41 (s, 1H), 6.75 (s, 1H), 4.57 (s, 2H); $^{13}$CNMR (150 MHz, DMSO-d6):

d=165.11, 154.81, 152.77, 149.39, 148.69, 144.66, 142.48, 139.34, 134.01, 132.70, 127.76, 127.27, 118.82, 117.24, 115.55, 112.47, 111.77, 110.13; HRMS (ESI-TOF): m/z calculated for $C_{23}H_{16}N_4O_2$: 381.1346 (M+H)+; found: 381.1358.

Synthesis of 7a

To a solution of 4-bromo-2-(4-cyanophenyl)pyridine (200 mg, 0.77 mmol.) in dry DME (3 mL) was added 4-aminocarbonyl phenyl boronic acid (152 mg, 0.80 mmol.) and water (1 mL). Then, $K_2CO_3$ (320 mg, 2.3 mmol.) and $Pd(PPh_3)_4$ (36 mg, 0.03 mmol.) were added and the reaction heated at 85° C. overnight. The reaction mixture was evaporated, adsorbed over silica gel and purified by column chromatography using EtOAc as eluent to afford 7a as a white solid (160 mg). $^1$HNMR (600 MHz, DMSO-d$_6$): d=8.82 (d, J=6 Hz, 1H), 8.45 (m, 3H), 8.13 (brs, 1H), 8.06 (m, 4H), 7.84 (d, J=6 Hz, 1H), 7.49 (brs, 1H); $^{13}$CNMR (150 MHz, DMSO-d$_6$): d=167.25, 154.98, 150.54, 147.61, 142.84, 139.54, 134.89, 132.69, 128.25, 127.66, 127.09, 121.28, 118.83, 111.60; HRMS (ESI-TOF): m/z calculated for $C_{19}H_{13}N_3O$: 300.1131 (M+H)+; found: 300.1132.

Synthesis of 7b

To a solution of 2-bromo-6-(furan-2-yl) pyridine (280 mg, 1.25 mmol.) in dry DME (3 mL) was added 4-cyanophenyl boronic acid (220 mg, 1.3 mmol.) and water (1 mL). Then, $K_2CO_3$ (520 mg, 3.75 mmol.) and $Pd(PPh_3)_4$ (60 mg, 0.05 mmol.) were added and the reaction heated at 85° C. overnight. The reaction mixture was evaporated, adsorbed over silica gel and purified by column chromatography using Hex/EtOAc (8:2) as eluent to afford 7b as a white solid (180 mg). $^1$HNMR (600 MHz, CDCl$_3$): d=8.23 (d, J=6 Hz, 2H), 7.86 (t, J=6 Hz, 1H), 7.80 (m, 1H), 7.73 (d, J=6 Hz, 1H), 7.66 (d, J=6 Hz, 1H), 7.59 (s, 1H), 7.22 (s, 1H), 6.60 (m, 1H); $^{13}$CNMR (150 MHz, CDCl$_3$): d=154.24, 153.10, 149.15, 143.11, 142.84, 137.26, 132.05, 127.04, 118.42, 117.52, 111.69, 108.78; HRMS (ESI-TOF): m/z calculated for $C_{16}H_{10}N_2O$: 247.0866 (M+H)+; found: 247.0866.

General Procedure for compounds 10a-c. To a solution of furancarboximidine 8 (250 mg, 1.72 mmol) in IPA (20 mL) was added Na (45 mg, 2 mmol) and the reaction was refluxed for 2 hrs. Afterwards, 2 (500 mg, 1.72 mmol) was added and the mixture was refluxed overnight. Then, it was evaporated to dryness under vacuum, dissolved in DCM:MeOH (8:2) and filtered through a pad of silica gel. The filtrate was evaporated to dryness to give a red oil. Carboxylic acid 9 was precipitated using EtOAc:Hex (1:1) as a yellow solid (55%). This material was carried on without further purification. 9 (200 mg, 0.55 mmol) was dissolved in DCM (20 mL) and oxalyl chloride (0.2 mL, 36 mmol) followed by 1 drop of DMF. The reaction was stirred at room temperature overnight. Solvent was removed in vacuo and the remaining solid was redissolved in DCM (50 mL). The solution was poured onto a $NH_4OH$ solution (50 mL) and the reaction mixture was stirred for 30 min. The organic layer was separated, dried and evaporated under vacuo to afford a brown oil which was purified to obtain pyrimidine 10.

10a: $^1$HNMR (600 MHz, DMSO-d6): d=8.66 (s, 1H), 8.65 (d, J=2 Hz, 2H), 8.55 (d, J=12 Hz, 2H), 8.18 (s, 1H), 8.10 (m, 4H), 8.03 (s, 1H), 7.60 (s, 1H), 7.55 (s, 1H), 6.79 (s, 1H); $^{13}$CNMR (150 MHz, DMSO-d6): d=167.24, 163.91, 162.60, 157.33, 151.72, 146.12, 140.41, 138.39, 136.65, 132.89, 128.20, 128.04, 127.35, 118.55, 114.35, 113.49, 112.61, 111.30; HRMS (ESI-TOF): m/z calculated for $C_{22}H_{14}N_4O_2$: 367.1189 (M+H)+; found: 367.1202.

10b: $^1$HNMR (400 MHz, DMSO-d6): d=8.35 (d, 2H), 8.22 (m, 1H), 8.10 (d, 2H), 7.82 (bs, 2H), 7.90 (m, 4H), 7.80 (d, 2H), 7.50 (m, 3H); HRMS (ESI-TOF): m/z calculated for $C_{22}H_{16}N_4O$: 377.1402 (M+H)+; found: 377.1482.

10c: $^1$HNMR (400 MHz, DMSO-d6): d=8.66 (s, 1H), 8.65 (d, J=2 Hz, 2H), 8.55 (d, J=12 Hz, 2H), 8.18 (s, 1H), 8.10 (m, 4H), 8.03 (s, 1H), 7.60 (s, 1H), 7.55 (s, 1H), 6.79 (s, 1H); HRMS (ESI-TOF): m/z calculated for $C_{22}H_{16}N_4O$: 382.1555 (M+H)+; found: 382.1482.

Biological Methods:

Protein expression and purification. His-tagged MYC, mMAX, MYC-MAX, and MAX-MAX constructs were expressed in BL21 E. coli cells and purified as previously described.[10]

FET functionalization and regeneration. FET experiments were conducted on an Agile R100 (Nanomedical Diagnostics) at ambient temperature. Chips were functionalized with Ni-NTA according to manufacturer protocols. Surface-bound Ni-NTA sites were then bound to His-tagged protein by 15 min incubation with ~100 nM protein in 50 mM MES (pH 6.0). Ni-NTA functionalized chips were regenerated via treatment with 250 mM imidazole for 30 mins, followed by extensive washing in MES, then reintroduction of His-tagged protein.

Relative binding studies. Test compounds were dissolved to desired concentration in MES (pH 6.0) buffer with 3% DMSO. Protein-bound chips were initialized and rinsed in MES buffer with 3% DMSO. For relative binding studies, 6-8 test compounds (including 5a) were analyzed at 10 μM in a single run, and the $R_{eq}$ determined and compared to that of 5a. Compounds were tested a minimum of three times across different chips.

MYC affinity assessment. The affinity of 5g was determined by finding the 12 $R_{max}$ for a concentration curve. Varying concentrations of 5g were allowed to equilibrate with MYC, and the $R_{eq}$ values plotted against the concentration. A logarithmic line fit for this data was determined by Microsoft Excel, and the concentration of 5g for ½ $R_{max}$ calculated from the equation for that line. This was repeated across three chips and the affinity averaged across those three runs.

Surface Plasmon Resonance. All experiments were conducted using a Biacore 3000 instrument (GE Healthcare) equipped with a research-grade SA sensor chip (BR1000032, GE Healthcare). Biotin-labeled EBOX DNA (Biotin-GTAGGCCACGTGACCGGG, Eurofins Operon) and unlabeled complementary strand at 10 μM were mixed and heated at 95° C. for 5 min, and then slowly cooled to room temperature for 20 min to anneal. Annealed EBOX dsDNA was diluted 100-fold in running buffer (1:10 HBS+ EP, BR-1006-69, GE Healthcare) and was injected over the SA chip for capture. A blank SA chip flow cell was used for the reference flow cell in the binding assay. Compounds were added to MYC-MAX dimers at 10 μM in running buffer with 1% DMSO. Protein and compound were incubated at room temperature for 15 mins. Samples were injected at 30 μL/min for 5 min. Binding to EBOX was monitored over 2.5 min. Chip was regenerated in 10 mM glycine HCl (pH 2.2) for 0.5 min.

CEF assay. ATG-MYC transfection of CEF cells was conducted as previously described.[10] Compounds were added from 1000× DMSO stocks to a final DMSO concentration <0.1% in medium.

Figure 2:
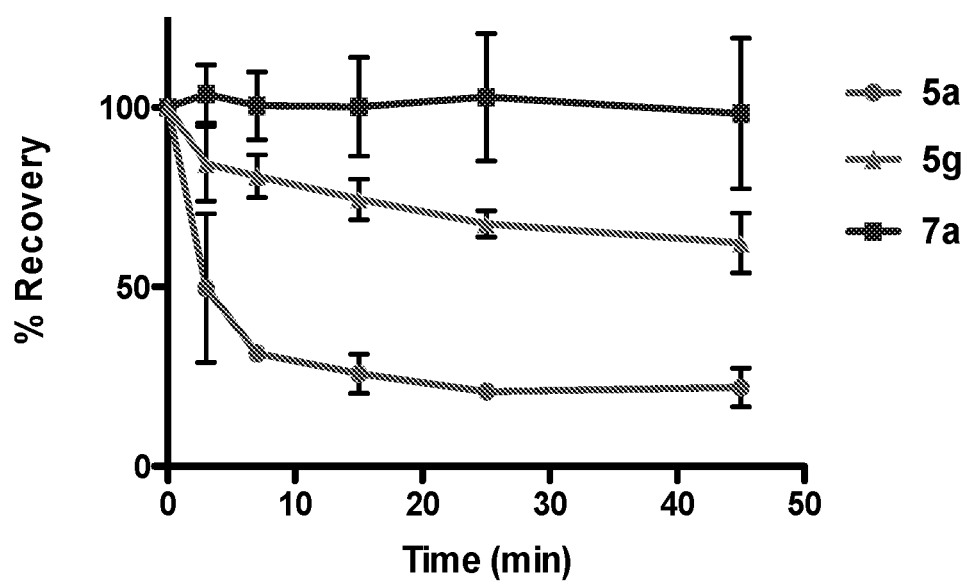
FIG. 2 shows oxidation susceptibility by rat liver microsomes by mass analysis. Compounds were incubated with microsomes at 37° C. for indicated time. Recovery calculated from AUC of extracted ion.

Furan analysis. Compounds 5a, 5g, and 7a were added to 0.5 mg/mL rat liver microsomes (pooled, Sigma-Aldrich) in PBS to a final concentration of 5 μM using <1.0% DMSO. Compounds were incubated at 37° C. 10 μL aliquots were removes at indicated time points and diluted 1:1000 in acetonitrile containing 1 μM TAP. Samples were analyzed on an Agilent 6100 Quadruple LC-MS system equipped with an Agilent ZORBAX SB-C8 column. Samples were run using $H_2O$+0.1% formic acid and MeCN+0.1% formic acid as the mobile phase. The percentage of $H_2O$+0.1% formic acid was linearly increased from 10-95% and the percentage of MeCN+0.1% formic acid was linearly decreased from 90-5% over a 7-minute run (500 μL/mL). Ion-extraction of the parent compound mass and integration was done using MassHunter software (Agilent). Normalization and averaging of runs were done using Microsoft Excel. Results of the analysis are shown in FIG. 2.

Solubility analysis. Compounds were analyzed for solubility by dynamic light scattering on a DynaPro NanoStar detector (Wyatt Technology). Compounds were dissolved in MES (pH 6.0) from a 1000×DMSO stock at varying concentrations. Samples were analyzed for aggregation and the maximal concentration at which aggregates were not observed was used as the measure of solubility.

PK analysis. Pharmacokinetic analysis of 5g was conducted by Explora Biolabs. 12 C57BL/6 (6 male, 6 female) mice were administered 5g at 10 mg/kg by IV injection. Blood samples were collected at 2 min and 0.08, 0.25, 0.5, 1, 2, 8 and 24 hours post-injection. Bioanalysis was conducted by Integrated Analytical Solutions by processing through a Shimadzu VP series 10 system LC followed by mass analysis on an Applied Biosystems/MDS SCIEX API 3000 triple quadrupole mass spectrometer. All procedures involving the care and use of animals was approved by the IACUC at Explora BioLabs.

What is claimed is:

1. A compound of formula (I)

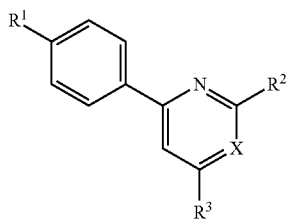

(I)

wherein
X is N or CH;
$R^1$ is thiazolyl;
$R^2$ is 2-furanyl;
$R^3$ is p-$C_6H_4$—$CONH_2$.

2. A pharmaceutical composition comprising an effective amount of a compound of formula (I)

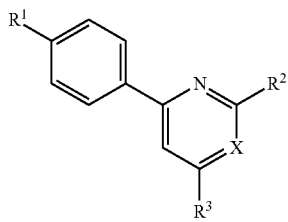

(I)

wherein
X is N or CH;
$R^1$ is thiazolyl;
$R^2$ is 2-furanyl;
$R^3$ is p-$C_6H_4$—CONH2; and pharmaceutically acceptable excipients.

3. A method for treating cancer, comprising administering an effective amount of a pharmaceutical composition comprising formula (I)

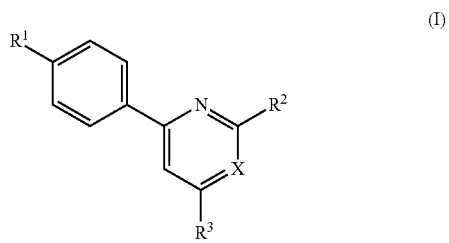

(I)

wherein
X is N or CH;
$R^1$ is thiazolyl;
$R^2$ is 2-furanyl; and
$R^3$ is p-$C_6H_4$—$CONH_2$.

4. A method of inhibiting MYC-MAX dimerization, comprising contacting MYC with an effective amount or concentration of a compound of claim 1.

5. A method of inhibiting transcriptional activation by MYC, comprising contacting MYC with an effective amount or concentration of a compound of claim 1.

6. A method of inhibiting MYC-induced cellular proliferation, comprising contacting MYC with an effective amount or concentration of a compound of claim 1.

7. The method of claim 3, wherein the cancer is associated with dysregulation or overexpression of c-Myc.

8. The method of claim 3, wherein the cancer is selected from the group consisting of brain tumors, spinal tumors, maxillary sinus cancer, cancer of the pancreatic gland, gum cancer, tongue cancer, lip cancer, nasopharyngeal cancer, mesopharyngeal cancer, hypopharyngeal cancer, laryngeal cancer, thyroid cancer, parathyroid cancer, lung cancer, pleural tumors, cancerous peritonitis, cancerous pleuritis, esophageal cancer, stomach cancer, colon cancer, bile duct cancer, gallbladder cancer, pancreatic cancer, hepatic cancer, kidney cancer, bladder cancer, prostate cancer, penile cancer, testicular tumors, cancer of the adrenal glands, uterocervical cancer, endometrial cancer, vaginal cancer, vulvar cancer, ovarian cancer, ciliated epithelial cancer, malignant bone tumors, soft-tissue sarcomas, breast cancer, skin cancer, malignant melanomas, basal cell tumors, leukemia, myelofibrosis with myeloid metaplasia, malignant lymphoma tumors, Hodgkin's disease, plasmacytomas, and gliomas.

9. The method of claim 3, wherein the composition or the pharmaceutical composition further comprises one or more known antitumor drugs, tumor metastasis-inhibitors, inhibitors for thrombogenesis, therapeutic drugs for joint destruction, analgesics, anti-inflammatory drugs, immunoregulators and/or immunosuppressants.

* * * * *